United States Patent
Bayram et al.

(10) Patent No.: US 9,810,646 B2
(45) Date of Patent: Nov. 7, 2017

(54) EDGE TREATMENT SYSTEM AND METHOD FOR EVALUATING A MATERIAL

(71) Applicant: PaneraTech, Inc., Chantilly, VA (US)

(72) Inventors: Yakup Bayram, Falls Church, VA (US); Alexander C. Ruege, Fairfax, VA (US); Eric K. Walton, Columbus, OH (US)

(73) Assignee: PANERATECH, INC., Chantilly, VA (US)

( * ) Notice: Subject to any disclaimer, the term of this patent is extended or adjusted under 35 U.S.C. 154(b) by 374 days.

(21) Appl. No.: 14/695,532

(22) Filed: Apr. 24, 2015

(65) Prior Publication Data

US 2015/0355109 A1    Dec. 10, 2015

Related U.S. Application Data

(60) Provisional application No. 61/984,360, filed on Apr. 25, 2014.

(51) Int. Cl.
*G01R 27/02* (2006.01)
*G01N 22/00* (2006.01)

(52) U.S. Cl.
CPC .................................. *G01N 22/00* (2013.01)

(58) Field of Classification Search
USPC ................................................ 324/637, 639
See application file for complete search history.

(56) References Cited

PUBLICATIONS

M. Bogosanovic, Microwave Sensing for Non-Destructive Evaluation of Anisotropic Materials with Application in Wood Industry, 2012, available at http://aut.researchgateway.ac.nz/handle/10292/4796.*
Bogosanovic et al., Microwave Nondestructive Testing of Wood Anisotropy and Scatter, IEEE Sensors Journal, vol. 13, No. 1, Jan. 2013.*
D. K. Ghodgaonkar et al., A free-space method for measurement of dielectric constants and loss tangents at microwave frequencies, IEEE Transactions on Instrumentation and Measurement, vol. 38, No. 3, pp. 789-793, Jun. 1989.*

* cited by examiner

*Primary Examiner* — Daniel Miller
(74) *Attorney, Agent, or Firm* — Whiteford, Taylor & Preston, LLP; Gregory M. Stone

(57) ABSTRACT

Disclosed is an improved system and method to treat an edge of a material for determining a property of such material through measurements of electromagnetic waves. The system and method are operative to mitigate the adverse effects caused by the interaction between an electromagnetic wave and an edge of a sample of a material under test. The system and method define a configuration to block and significantly attenuate the propagation of electromagnetic waves that may reach an edge of the sample being evaluated. This configuration reduces the undesired effects caused by edge-diffraction that may interfere with the measurement of desired electromagnetic waves for material evaluation. As a result, a property of a material under test can be measured more accurately, especially near the edges of such material. In addition, the system and method enable the evaluation of a small-size sample of a material.

19 Claims, 9 Drawing Sheets

EDGE TREATMENT SYSTEM AND METHOD FOR EVALUATING A MATERIAL

CROSS REFERENCE TO RELATED APPLICATIONS

This application is based upon and claims priority from U.S. Provisional Patent Application Ser. No. 61/984,360 entitled "Edge Treatment for Accurate RF Measurement of Materials Near Edges" filed with the U.S. Patent and Trademark Office on Apr. 25, 2014, by the inventors herein, the specifications of which is incorporated herein by reference.

GOVERNMENT LICENSE RIGHTS

This invention was made with Government support under Contract No FA8650-12-M-5144. The Government may have certain rights in the invention.

FIELD OF THE INVENTION

The present invention relates generally to systems and methods for evaluating a material through measurements of transmitted energy. More particularly, the present invention relates to systems and methods for determining a property of a material based on measurements of electromagnetic waves.

BACKGROUND OF THE INVENTION

Material characterization systems using electromagnetic waves are available to measure certain properties of a material. The reflectivity, transmissivity, and absorptivity of electromagnetic waves impinging upon a sample of a material can be measured to determine important attributes of such material, including surface characteristics, internal homogeneity, insertion loss, dielectric permittivity, loss tangent, shielding effectiveness, and even manufacturing defects. However, where the measurement area of the sample under evaluation is near an edge of the material, the electromagnetic waves interact with the edge of the material and may corrupt the measurements.

Edge treatment systems and methods exist for mitigating the effects of the interaction of electromagnetic waves with the edge of a material. In particular, attenuation of the reflection of electromagnetic radiation in a given frequency range by means of an edge treatment based on a structure of properly-spaced long strips of electrically loaded conductive material and a dielectric spacer has been addressed in the prior art, as described in U.S. Pat. No. 6,184,815 to Carlson. However, this treatment is based on forming a transmission line between these strips and the treated material to match the impedance of the material to free space. Thus, the effectiveness of this approach is limited to treating relatively high-conductive materials, requires a spacing between the edge treatment structure and the treated material, and may not be suitable for small-size samples.

Primarily, the applications of material evaluation systems based on propagating electromagnetic waves include material characterization, calibration, and general purpose measurements. Therefore, edge-diffraction of the electromagnetic waves impinging upon a sample under test may lead to inaccuracies that render measurements worthless. As a result, in order to minimize these edge effects, a number of limitations may be imposed on the capabilities of the material evaluation system, such as the frequency range of operation, the size and area of the sample under test, the sophistication and complexity of the components of the system, and the quality control of a material under production. Thus, an edge treatment technique that allows accurate measurements of a material to overcome these limitations are key in terms of costs and operational functionality of users.

Currently, there is no well-established method of accurately characterizing a sample of a material under evaluation near the edges of such material, using electromagnetic waves. Such solutions are particularly lacking in industrial applications wherein the quality of a material under production must be monitored continuously to guarantee a level of performance from edge-to-edge. As a consequence, multiple material evaluation methods may be necessary to implement or a substantially lower productivity may result. Furthermore, lower product quality and larger tolerances in the performance characteristics of a material may be expected. Likewise, the cost of production of high-quality material may significantly increase.

Previous efforts have been made to suppress diffraction of electromagnetic waves from an edge, as described in U.S. Pat. No. 8,035,568 to Diaz et al., U.S. Pat. No. 5,963,176 to Solheim et al., and U.S. Pat. No. 5,298,911 to Li. However, these efforts have faced certain challenges and limitations for material evaluation applications. In particular, attempts made to reduce edge-diffraction from antenna surfaces have been generally unsuccessful for material evaluation applications because of the narrow frequency bandwidth, large size, or the need to physically modify or have a relatively high-conductive material under test. Such previous efforts have been particularly lacking in the evaluation of a small-size sample of a material where all edges of the sample may interact with the electromagnetic waves used during measurements.

Thus, there remains a need in the art for improved systems and methods for treating the edges of a material under evaluation, through measurements of propagating electromagnetic waves, that avoid the problems of prior art systems and methods.

SUMMARY OF THE INVENTION

An improved system and method to treat an edge of a material for determining a property of such material through measurements of electromagnetic waves is disclosed herein. One or more aspects of exemplary embodiments provide advantages while avoiding disadvantages of the prior art. The system and method are operative to mitigate the adverse effects caused by the interaction between an electromagnetic wave and an edge of a sample of a material under test. The system and method define a configuration to block and significantly attenuate the propagation of electromagnetic waves that may reach an edge of the sample being evaluated. This configuration reduces the undesired effects caused by edge-diffraction that may interfere with the measurement of desired electromagnetic waves for material evaluation. As a result, a property of a material under test can be measured more accurately, especially near the edges of such material. In addition, the system and method enable the evaluation of a small-size sample of a material, wherein transmitted electromagnetic waves required for evaluating such sample would unavoidably interact with at least one edge of the sample under test.

The system includes one or more structures configured and positioned to significantly reduce the electromagnetic waves that may reach an edge of a material being evaluated. These undesired electromagnetic waves may either directly or by exciting surface waves that propagate along the surface of the sample reach an edge of such sample. This may create an interference with desired electromagnetic waves transmitted through or reflected from the sample. The edge treatment system primarily blocks direct, undesired electromagnetic waves and attenuates undesired surface waves. This is particularly important where evaluation of a small-size sample or near the edges of a material is required.

The method of treating an edge of a material under evaluation, using electromagnetic waves, includes the steps of setting up a sample of a material under test and determining the area of the sample to be evaluated. The method further includes the steps of identifying "compromised" areas of the sample under test and selecting and setting up the edge treatment system configuration for these areas.

The method also includes performing transmission and reflection measurements of both the sample under test and other reference materials, calibrating measured data of the sample under test with calibration data from the measurements of the reference materials, and extracting the desired parameters corresponding to one or more properties of the sample of the material under test, by performing data processing and evaluation of calibrated data.

By significantly reducing the effects of edge-diffraction caused by the interaction of electromagnetic waves with the sample of a material under test, as compared to standard techniques, the system and method are able to greatly improve the accuracy of measurements of small-size samples and areas near the edge of a material being evaluated.

BRIEF DESCRIPTION OF THE DRAWINGS

The numerous advantages of the present invention may be better understood by those skilled in the art by reference to the accompanying drawings in which.

DETAILED DESCRIPTION OF THE INVENTION

The following description is of one or more particular embodiments of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
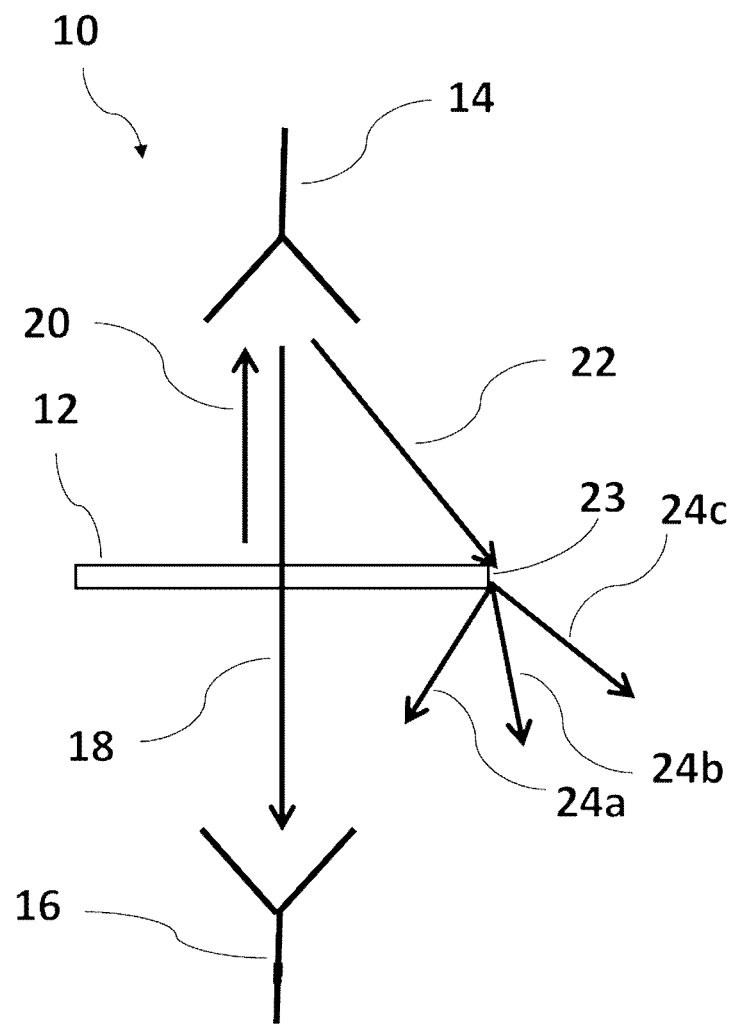
FIG. 1 shows a material characterization system, based on the transmission of electromagnetic waves.

FIG. 1 shows a material characterization system 10, based on the transmission of electromagnetic waves. The system is configured to characterize a material such as a rectangular layer or film of a sample of a material under test 12. In general, material characterization system 10 comprises a transmit antenna 14 and a receive antenna 16 aligned with respect to each other, such that receive antenna 16 is able to receive electromagnetic waves, transmitted by transmit antenna 14, preferably at a maximum level of power.

Transmit antenna 14 radiates electromagnetic waves or signals toward receive antenna 16. In general, sample 12 is mounted on a mounting tray (not shown) that is part of material characterization system 10. Likewise, sample 12 is disposed in between and equidistant from antennas 14 and 16 and substantially perpendicular to the propagation path of a direct signal 18 transmitted by transmit antenna 14 to receive antenna 16. Thus, direct signal 18 is received by receive antenna 16 through sample 12. In addition, a reflected signal 20 is reflected back to transmit antenna 14 after impinging upon sample 12.

Typically, material characterization system 10 measures direct signal 18 and reflected signal 20 for system calibration or for characterization of a material. During system calibration measurements, sample 12 consists of a reference material such as a highly conductive material, air, or other previously characterized or known material. During characterization measurements, sample 12 consists of a material to be characterized.

In general, material characterization system 10 characterizes sample 12 by measuring direct signal 18 and reflected signal 20, and then comparing these measurements to the corresponding measurements of a known reference material, to determine a property of sample 12, such as transmissivity, reflectivity, or absorptivity. In turn, more specific properties of a material can be derived from these measurements, including transparency, surface resistivity, conductivity, dissipation loss, magnetic permeability, and dielectric permittivity.

However, as shown in FIG. 1, a transmitted electromagnetic wave 22 may generate a number of diffracted electromagnetic waves, such as signals 24a, 24b, and 24c that may interfere with a measurement of material characterization system 10, i.e. the measurement of direct signal 18 and reflected signal 20. Diffracted signals 24a, 24b, and 24c may be generated as a result of electromagnetic wave propagation effects, including, primarily, from the interaction of transmitted electromagnetic wave 22 with edge 23 of sample 12 and, secondarily, from the excitation of a surface electromagnetic wave on sample 12 that reaches edge 23, or a combination of both.

In general, diffracted signals 24a, 24b, or 24c received by receive antenna 16 interfere with direct signal 18. Likewise, diffracted signals 24a, 24b, or 24c received by transmit antenna 14 interfere with reflected signal 20. These interferences may corrupt the measurements of material characterization system 10 up to a level that render the characterization of a material useless.

Therefore, material characterization system 10 may not be able to characterize sample 12 where edge-diffracted signals 24a, 24b, or 24c reach transmit antenna 14 or receive antenna 16. Thus, it is important to reduce the level of diffracted signals 24a, 24b, and 24c to properly characterize sample 12. In particular, in order to optimize sample characterization, it is important to mitigate the level of diffracted signals 24a, 24b, and 24c that are received by receive antenna 16.

Figure 2A:
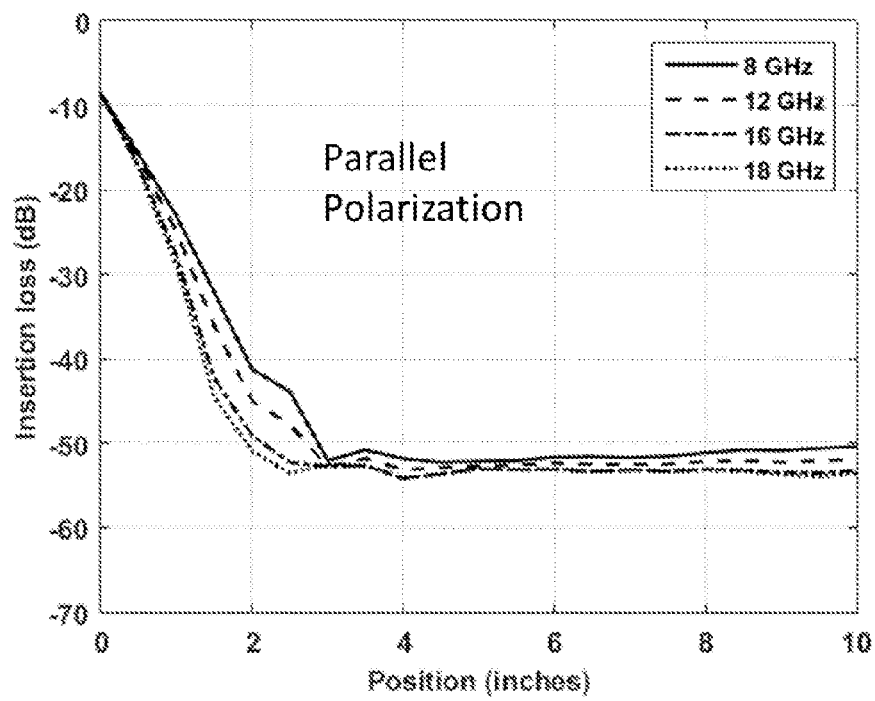
FIGS. 2A and 2B show the results of the measurements of the insertion loss of a material under test using a material characterization system.
Figure 2B:
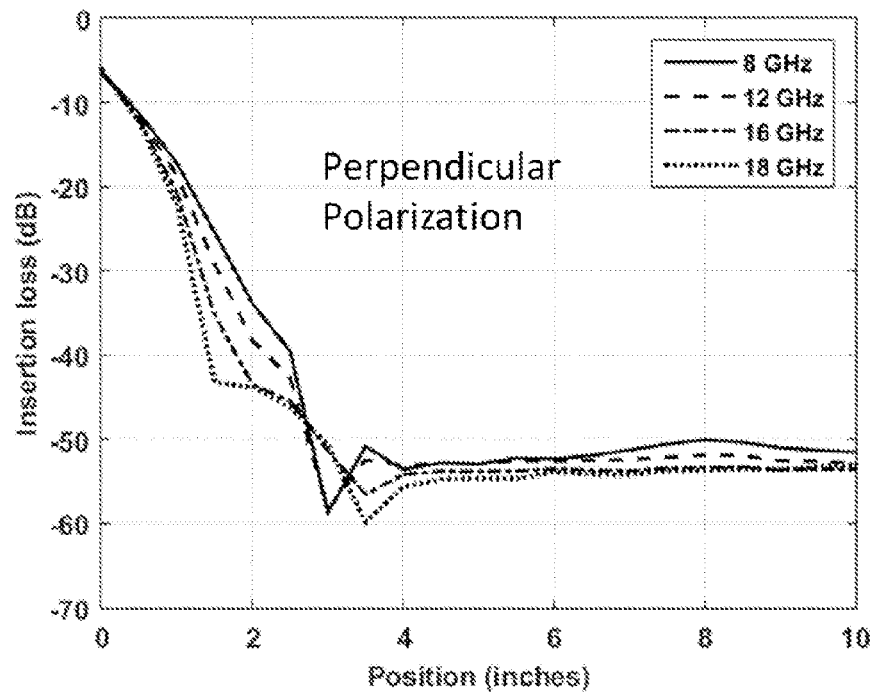

FIGS. 2A and 2B show the results of the measurements of the insertion loss of a sample 12 with no edge treatment, using material characterization system 10. In this case, sample 12 consists of a 24-inch wide by 48-inch long rectangular substrate film of approximately 10 mils in thickness, comprising a coating layer of Indium Tin-Oxide (ITO) of about 0.2 mils, with a rectangular cross-sectional profile. Sample 12 is set up such that at the zero position edge 23 is aligned with the center of the illumination spot of transmit antenna 14 and receive antenna 16 on sample 12. Sample 12 is moved such that transmit antenna 14 and receive antenna 16 illuminate an area of interest of sample 12 to be measured.

Those skilled in the art will recognize that alternatively at least one of transmit antenna 14 and receive antenna 16 or a combination of sample 12 and at least one of transmit antenna 14 and receive antenna 16 may be moved to scan the area of interest of sample 12 to be measured.

In FIGS. 2A and 2B, the insertion loss values are plotted as a function of the distance from edge 23 of sample 12 to the center of the illumination spot of transmit antenna 14 and receive antenna 16 on the surface of sample 12, for the set of 8; 12; 16; and 18 GHz frequencies. In particular, FIG. 2A shows the measurements corresponding to a parallel polarization, whereas FIG. 2B shows the results for a perpendicular polarization. As used herein, "parallel" polarization is also intended to refer to an electromagnetic wave 22 having the electric field component varying in time along an axis that is both parallel to edge 23 and substantially parallel to sample 12. Likewise, "perpendicular" polarization is also intended to refer to an electromagnetic wave 22 having the electric field component varying in time along an axis that is both perpendicular to edge 23 and substantially parallel to sample 12.

Transmit antenna 14 and receive antenna 16 each consists of a polyrod probe antenna, operating in the 8 to 18 GHz frequency range and having a corresponding circular spot size ranging from 3.5 inches to 1.1 inches in diameter at 1.5 inches from the antenna. More specifically, transmit antenna 14 and receive antenna 16 are placed approximately 4 inches apart, equidistant from sample 12.

During measurements, sample 12 is moved along its width from a position wherein antennas 14 and 16 align with edge 23 (zero position) to a region around the center of sample 12, wherein the spot size of antennas 14 and 16 on sample 12 does not interact with any edges of sample 12. Specifically, the type of material used as sample 12 was selected, for validation purposes, to have a reference material having a well-known substantially uniform insertion loss, with average variations within 2 dB or 3 dB. However, as shown in FIGS. 2A and 2B, insertion loss variations of several tens of dB occur for positions approaching edge 23. Thus, the effects of edge 23 in the insertion loss measurement are significant, rendering these type of measurements useless for characterizing sample 12 around edge 23.

As shown in FIGS. 2A and 2B, the distortion of measurements near edge 23 depends on the polarization and frequency of operation. More specifically, FIG. 2A shows that for parallel polarization, measurements are significantly affected in regions of sample 12 within 3 inches of edge 23. Furthermore, FIG. 2B shows that for perpendicular polarization, measurements may be critically affected in regions of sample 12 up to 4 inches away from edge 23. Likewise, measurements at lower frequencies are more sensitive for both parallel and perpendicular polarizations within the set of measured frequencies.

Figure 3:
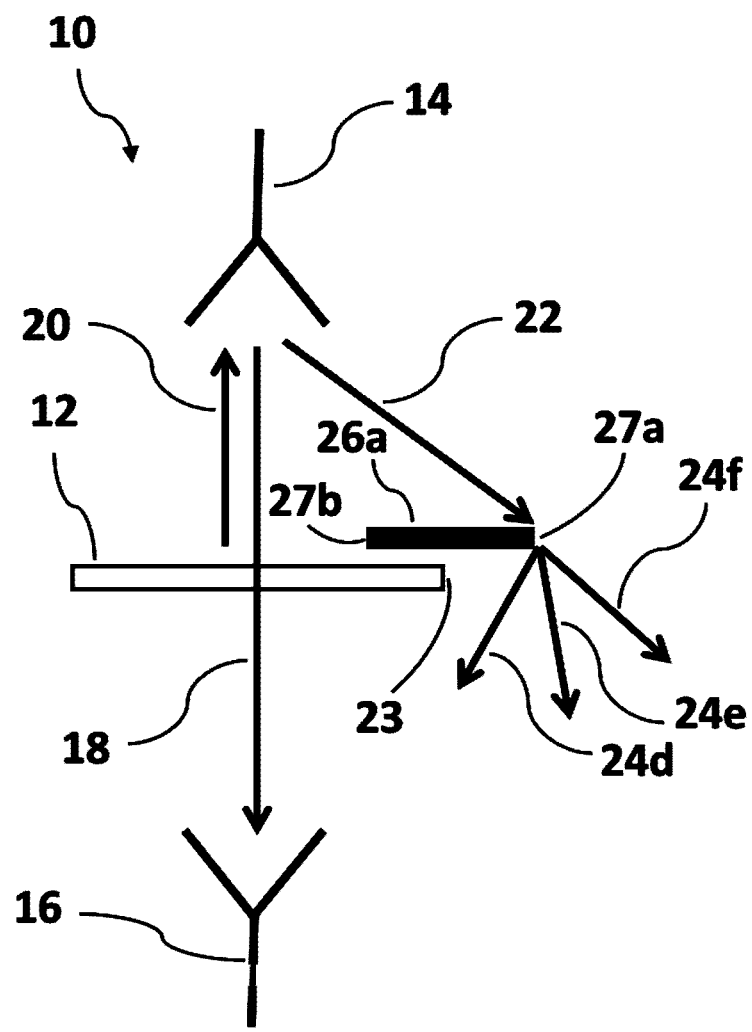
FIG. 3 shows a material characterization system setup, wherein a material under test is subjected to a single edge treatment.

In accordance with certain aspects of an embodiment of the invention, FIG. 3 shows a setup of material characterization system 10, wherein a substrate or layer of edge treatment material 26a is disposed in between edge 23 and transmit antenna 14 at a distance of approximately 0.25 inches from edge 23. Additionally, edge treatment material 26a is disposed substantially parallel to sample 12.

The purpose of edge treatment material 26a is to prevent transmitted electromagnetic wave 22 from reaching edge 23 of sample 12. Thus, material 26a is preferably non-transparent at the frequencies of operation of material characterization system 10, and may include, by way of non-limiting examples, materials such as a conductive material, a material having a variable conductivity, an electromagnetic metamaterial, a magnetic absorber material, a radiofrequency absorber material, or any combination thereof configured in different geometrical arrangements, to block or significantly attenuate the propagation of wave 22 through material 26a. More preferably, material 26a comprises a highly conductive material, such as a metal plate of aluminum, which prevents wave 22 from directly interacting with edge 23.

The effectiveness of using edge treatment in material characterization system 10 depends on several factors, including the overlap area of edge treatment material 26a with sample 12, any gaps between edge treatment material 26a and sample 12, the shape of edge treatment material 26a, and the polarization of transmitted electromagnetic wave 22.

In the configuration shown in FIG. 3, edge treatment material 26a has a first edge 27a non-overlapping sample 12 and a second edge 27b overlapping sample 12. Thus, edge treatment material 26a is disposed such that edge 23 of sample 12 is positioned in between and non-overlapping edges 27a and 27b. As a result, a number of diffracted electromagnetic waves, such as signals 24d, 24e, and 24f, still create some level of interference (although reduced, as discussed below) with a measurement of material characterization system 10.

Diffracted signals 24d, 24e, and 24f may be generated as a result of electromagnetic wave propagation effects, including primarily from the interaction of transmitted electromagnetic wave 22 with edge 27a of edge treatment material 26a, and secondarily from the excitation of a surface electromagnetic wave on edge treatment material 26a that reaches edge 27a, or a combination of both. In addition, the excitation of a surface electromagnetic wave on sample 12 or the excitation of an electromagnetic wave in a waveguide mode between sample 12 and edge treatment material 26a, reaching edge 23 may generate diffracted waves 24a, 24b, and 24c, as correspondingly shown in FIG. 1.

However, although diffracted signals 24a, 24b, 24c, 24d, 24e, and 24f may reach receive antenna 16 and interfere with direct signal 18, the level of interference will be lower than in the case where no edge treatment is used. This reduction is due to the suppression of the main diffraction effect caused by the interaction of electromagnetic wave 22 with edge 23. Also, because the distance from transmit antenna 14 and receive antenna 16 to edge 27a is larger than the corresponding distances to edge 23, the diffraction effects resulting from the interaction of electromagnetic wave 22 with edge 27a are lower than the diffraction effects caused by the interaction of electromagnetic wave 22 with edge 23 where no edge treatment is used.

More specifically, in the configuration shown in FIG. 3, edge treatment material 26a consists of a rectangular aluminum plate of about 3 inches in width, 6 inches in length, and 0.0625 inches in thickness, separated approximately 0.25 inches from sample 12, and disposed such that edges 27a and 27b of material 26a are substantially parallel to edge 23 of sample 12. Material 26a partly overlaps sample 12, such that the distance from edge 23 to the projected line of edge 27b over sample 12 is approximately 0.5 inches. The aluminum plate is mounted on a supporting structure, consisting of a metal base, to maintain mechanical stability of the plate during measurements. Furthermore, the base is positioned such that the plate is disposed in between transmit antenna 14 and the base. Moreover, the plate is mechanically attached with two metal screws to the base. Most preferably, the dimensions of the base are such that transmitted electromagnetic wave 22 does not directly interact with the base. In other words, the base is not within the field of view of transmit antenna 14, because the metal plate shields the base from electromagnetic wave 22. Thus, the base may be made of any type of material as long as the plate fully shields electromagnetic wave 22 that would impinge upon the base.

Alternatively, the supporting structure may be mechanically attached to the mounting tray of material characterization system 10, by means well-known in the prior art. Those skilled in the art will realize other ways of attaching the supporting structure to the mounting tray of material characterization system 10 or to edge treatment material 26a, such as by means of glue, adhesive, soldering, clamps, hooks, fasteners or a hinge, swivel, or rotary joint mechanism. Likewise, the base may be made of or be covered with a radiofrequency absorbing material in areas of the base wherein the plate does not shield electromagnetic wave 22.

The overlapping of edge treatment material 26a and sample 12 prevents an electromagnetic wave transmitted by transmit antenna 14 from directly reaching edge 23. In general, this overlapping is preferred to be within a range of between one twentieth of a wavelength and three quarters of a wavelength, corresponding to the largest frequency of the transmitted electromagnetic waves. Furthermore, material 26a extends away from sample 12, preferably by at least one wavelength corresponding to the largest frequency of the transmitted electromagnetic waves, to increase the distance from edge 27a to transmit antenna 14 and receive antenna 16, as compared to the distance from edge 23 to transmit antenna 14 and receive antenna 16.

Preferably, edge treatment material 26a is disposed in non-contact with sample 12 to allow free motion of sample 12 while operating material characterization system 10. This is particularly important in industrial settings where a material is characterized or monitored during production of a material continuously in motion. A specific separation gap between edge treatment material 26a and sample 12 depends on the specific type of material characterization system 10 used, and the type of sample 12 to be characterized. More specifically, where the thickness of sample 12 is not negligible, the separation gap between edge treatment material 26a and sample 12 corresponds to the distance from the surface of edge treatment material 26a closest to sample 12 to the surface of sample 12 closest to edge treatment material 26a.

A gap no larger than three quarters of a wavelength, corresponding to the largest frequency of the transmitted electromagnetic waves, is preferred to reduce the amount of overlapping between material 26a and sample 12 required to prevent signals to reach edge 23 of sample 12. Furthermore, a non-contact configuration between material 26a and sample 12 helps reduce the wearing effects on sample 12.

However, those skilled in the art will recognize that edge treatment material 26a may be disposed in physical contact with sample 12. This might be advantageous in certain settings where sample 12 is not required to move, such as in a laboratory setup, and is held in place with edge treatment material 26a. Likewise, shapes other than a rectangular shape of sample 12 and a rectangular cross-sectional profile and shape of edge treatment material 26a may be used, including circular, elliptical, triangular, polygonal, or even irregular shapes. In particular, the cross-sectional profiles and shapes of edge treatment material 26a and sample 12 do not need to be the same.

Furthermore, those skilled in the art will also recognize the edges of sample 12 and edge treatment material 26a need not be substantially parallel. Moreover, edge treatment material 26a does not need to fully overlap one or more edges of sample 12. Preferably, edge treatment material 26a is applied to at least a portion of edge 23 of sample 12 that is within the field of view of transmit antenna 14 during measurements. Thus, where sample 12 has an area equal or smaller than the spot size or footprint of a radiation pattern of transmit antenna 14 over sample 12, such that all edges of sample 12 are within the field of view of transmit antenna 14, edge treatment material 26a is preferably applied to all edges of sample 12.

Figure 4:
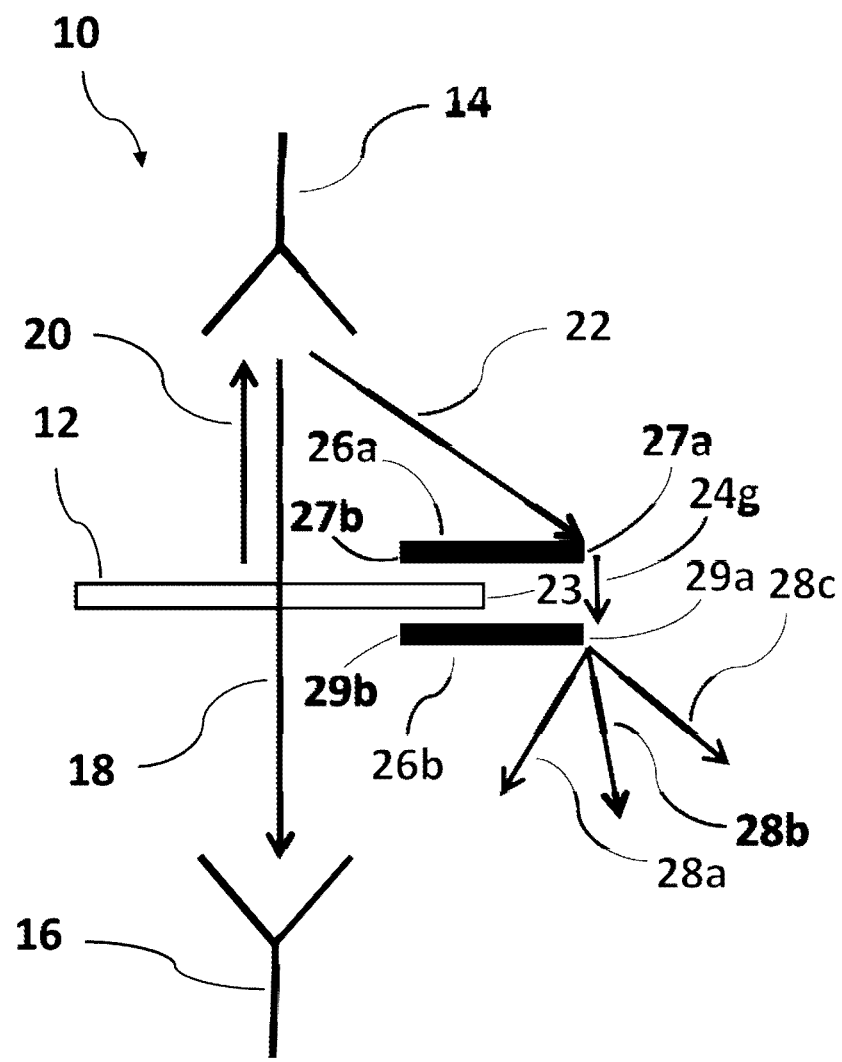
FIG. 4 shows a material characterization system setup, wherein a material under test is subjected to a dual edge treatment.

In an alternative configuration, FIG. 4 shows a setup of material characterization system 10, wherein an edge treatment comprises a first substrate or edge treatment material 26a and a second substrate or edge treatment material 26b. First edge treatment material 26a is disposed in between edge 23 of sample 12 and transmit antenna 14, similar to the configuration shown in FIG. 3. Second edge treatment material 26b is disposed in between edge 23 of sample 12 and receive antenna 16.

The purpose of second edge treatment material 26b is to prevent both a diffracted electromagnetic wave 24g from edge 27a of edge treatment material 26a and any edge-diffraction effects from edge 23 to directly reach receive antenna 16. Thus, material 26b is also preferably non-transparent at the frequencies of operation of material characterization system 10, having similar characteristics to those of material 26a.

In the configuration shown in FIG. 4, edge treatment material 26b preferably has the same shape and dimensions of edge treatment material 26a, as described in FIG. 3. Moreover, edge treatment material 26b is preferably positioned at the same distances to sample 12 and to edge 23 as is edge treatment material 26a. In other words, edge treatment material 26b is preferably a mirror image of edge treatment material 26a with respect to sample 12.

Accordingly, edge treatment material 26b is disposed substantially parallel to sample 12 and has a first edge 29a, non-overlapping sample 12, and a second edge 29b overlapping sample 12. Thus, edge treatment material 26b is disposed such that edge 23 of sample 12 is positioned in between and non-overlapping edges 29a and 29b. As a result, a number of diffracted electromagnetic waves, such as signals 28a, 28b, and 28c may interfere with a measurement of material characterization system 10.

Diffracted signals 28a, 28b, and 28c may be generated as a result of electromagnetic wave propagation effects, including primarily from the interaction of diffracted electromagnetic wave 24g with edge 29a of edge treatment material 26b, and secondarily from the excitation of a surface electromagnetic wave on edge treatment material 26b that reaches edge 29a of edge treatment material 26b, or a combination of both. In addition, the excitation of a surface electromagnetic wave on edge treatment material 26b that reaches edge 29b may also generate edge-diffraction effects affecting receive antenna 16.

However, although diffracted signals 28a, 28b, and 28c may reach receive antenna 16 and interfere with direct signal 18, the level of interference will be lower than in the case where only first edge treatment material 26a is used. This reduction is due to the suppression of the main diffraction effect on receive antenna 16, caused by the interaction of electromagnetic wave 22 with edge 27a. Also, because transmit antenna 14 is not in line-of-sight with and farther away from edge 29a as compared to edge 27a, the diffraction effects resulting from the interaction of diffracted electromagnetic wave 24g with edge 29a are lower than the diffraction effects caused by the interaction of electromagnetic wave 22 with edge 27a where only first edge treatment material 26a is used.

Thus, in this particular configuration, edge treatment materials 26a and 26b each consists of a rectangular aluminum plate of about 3 inches in width, 6 inches in length, and 0.0625 inches in thickness, separated approximately 0.25 inches from sample 12, and disposed such that edges 27a and 27b of material 26a and edges 29a and 29b of material 26b are substantially parallel to edge 23 of sample 12. Each plate partly overlaps sample 12, such that the distance from edge 23 to both the projected line of edge 27b over sample 12 and the projected line of edge 29b over sample 12 is approximately 0.5 inches.

Moreover, each plate attaches to a plastic block of about 1.5 inches in width, 3 inches in length, and 1 inch in thickness, by means of two metal screws inserted in holes along the thickness of the block. The plastic block is disposed in between the plates such that the plates are separated by the thickness of the block and the length of the block is substantially parallel to edges 27a, 27b, 29a, and 29b. The plastic block serves as a spacer between the two plates and provides mechanical stability to the two-plate assembly.

The two-plate assembly is mounted on a supporting structure, consisting of a metal base, to maintain mechanical stability of the two-plate assembly during measurements. Furthermore, the base is positioned such that the two-plate assembly is disposed in between transmit antenna 14 and the base. More specifically, the two-plate assembly is disposed such that sample 12 is in between the two plates, approximately equidistant from each plate, and non-overlapping the plastic block.

In addition, the two-plate assembly is mechanically attached with two metal screws to the base. Most preferably, the dimensions of the base are such that transmitted electromagnetic wave 22 does not directly interact with the base. In other words, the base is not within the field of view of transmit antenna 14, because the metal plates shield the base from electromagnetic wave 22. Thus, the base may be made of any type of material as long as the plates fully shield electromagnetic wave 22 that would impinge upon the base.

Likewise, because the plastic block is sandwiched between the two aluminum plates, the plastic block could be substituted by a block made of any type of material.

Those skilled in the art will recognize other ways of attaching edge treatment materials 26a and 26b to each other, such as by means of a straight, L-shaped or U-shaped arm, a flange, one or more screws, fasteners, hooks, gears, etc. A preferred attachment mechanism includes a manner to have an adjustable spacing between materials 26a and 26b, including a gear mechanism, calibrated screws, and knobs. More preferably the attachment mechanism also is reconfigurable to adapt to different settings of spacing, overlapping areas, positioning, and placing sample 12 in between materials 26a and 26b. Most preferably, the attachment mechanism has a first section attached to material 26a and a second section attached to material 26b, such that these two parts join by means of a hinge, a swivel, or a rotary joint.

Also, those skilled in the art will realize that edge treatment materials 26a and 26b may have alternative cross-sectional profiles and shapes, including circular, elliptical, triangular, polygonal, or even irregular shapes. Also, edge treatment materials 26a and 26b may be positioned differently, such that one does not necessarily represent a mirror image of the other one with respect to sample 12. Moreover, the shapes of edge treatment material 26a and edge treatment material 26b do not need to be the same. In this case, complementary shapes may be preferred; for instance, edge treatment materials 26a and 26b may have shapes wherein a cutoff in an area of edge treatment material 26a through which an electromagnetic wave coming from transmit antenna 14 may propagate is blocked by edge treatment material 26b.

Likewise, a cutoff in an area of second edge treatment material 26b through which an electromagnetic wave may propagate to receive antenna 16 is preferably blocked by edge treatment material 26a. More preferably, first edge treatment material 26a and second edge treatment material 26b have shapes and are disposed such that both may block a path of an electromagnetic wave coming from transmit antenna 14 that may interfere with direct signal 18 received by receive antenna 16.

Figure 5:
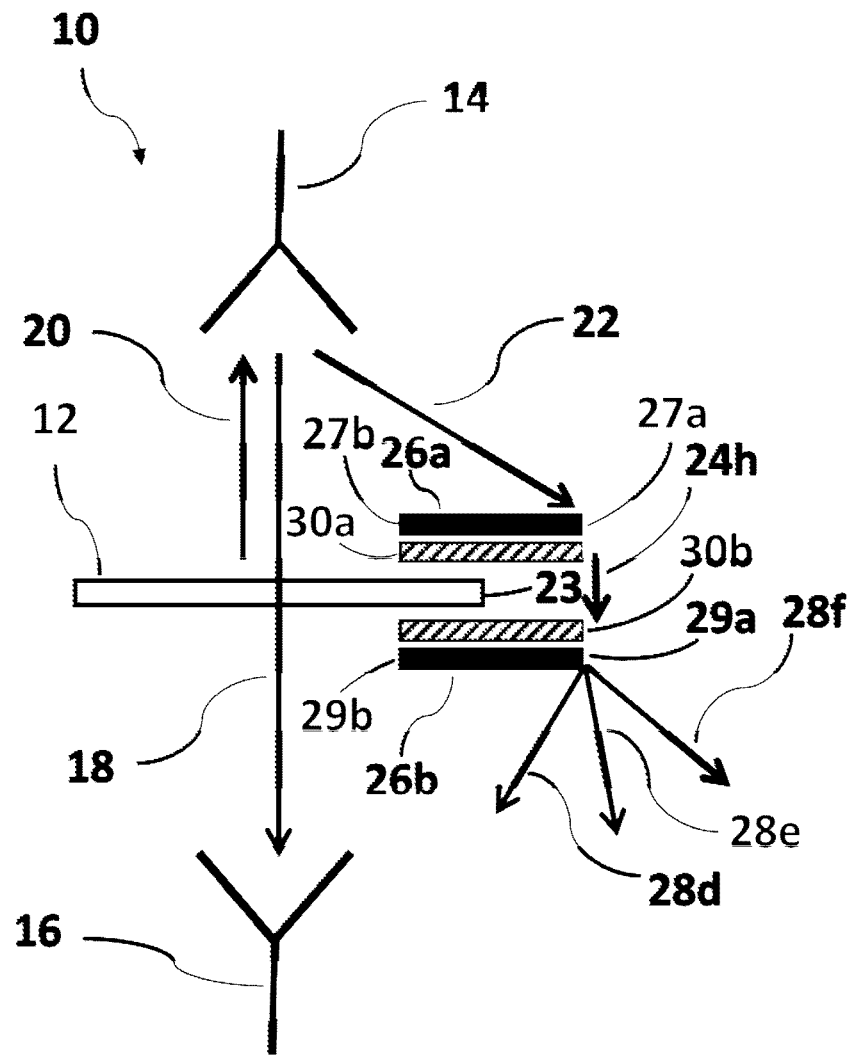
FIG. 5 shows a material characterization system setup, wherein a material under test is subjected to a dual edge treatment, and each edge treatment comprises two materials.

In yet another configuration, as shown in FIG. 5, a setup of material characterization system 10 includes an edge treatment system comprising a first edge treatment that consists of a combination of material 26a and a material 30a, disposed in between edge 23 of sample 12 and transmit antenna 14, and a second edge treatment that consists of a combination of material 26b and a material 30b, disposed in between edge 23 of sample 12 and receive antenna 16. The purpose of combining material 26a with material 30a and material 26b with material 30b is to further mitigate the possible interference resulting from edge diffraction from edge 27a of material 26a and from edges 29a and 29b of material 26b.

In this configuration, edge treatment materials 26a and 26b may have the same shape, dimensions, and positioning, as described in FIG. 4. Furthermore, edge treatment materials 30a and 30b each may have the same shape, width, and length as edge treatment materials 26a and 26b, respectively. In addition, edge treatment material 30a is disposed in between edge treatment material 26a and sample 12. Likewise, edge treatment material 30b is disposed in between edge treatment material 26b and sample 12.

Preferably, at the frequency of operation of material characterization system 10, materials 26a and 26b are highly conductive and materials 30a and 30b are highly absorbing. Thus, although a number of electromagnetic diffracted waves, such as signals 28d, 28e, and 28f may reach receive antenna 16 and interfere with direct signal 18, the level of interference will be lower than in the case where only single materials 26a and 26b are used as a first edge treatment and a second edge treatment, respectively.

This reduction is due to two main reasons. First, additional mitigation of the diffraction effects caused by the interaction of electromagnetic wave 22 with edge 27a occurs as a result of using material 30a, producing a more attenuated diffracted electromagnetic wave 24h; and second, a further attenuation of wave 24h occurs as a result of using material 30b, before wave 24h interacts with edge 29a. In addition, the use of materials 30a and 30b next to sample 12 helps in reducing small gaps between sample 12 and conductive materials 26a and 26b. As a result, the effects of any surface electromagnetic wave excited on sample 12 and materials 26a, 26b, 30a, and 30b will be smaller as compared to the case where only single materials 26a and 26b are used as a first edge treatment and a second edge treatment, respectively.

In a preferred configuration, materials 26a and 26b each consists of a metal plate of aluminum having 5 inches in width, 6 inches in length, and 0.0625 inches in thickness. On the other hand, materials 30a and 30b each preferably comprises a magnetic absorber material, such as the Emerson & Cuming ECCOSORB MCS, having 5 inches in width, 6 inches in length, and 0.04 inches in thickness. More specifically, materials 30a and 30b are flexible, magnetically loaded, high-loss rubber absorbers and are attached to materials 26a and 26b by means of a pressure sensitive adhesive or silicone-based adhesive that is commercially available.

Figure 6A:
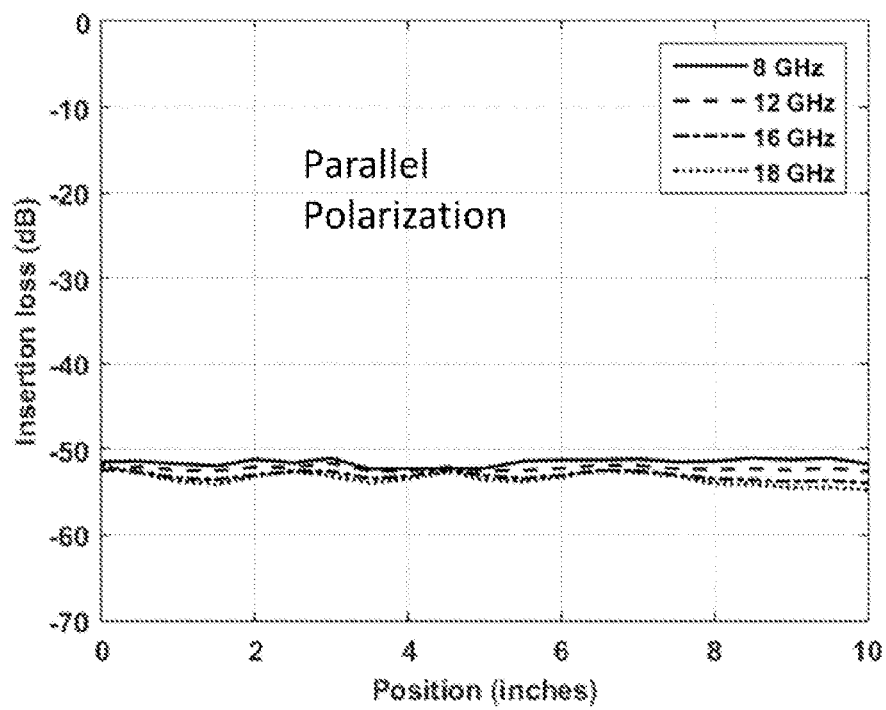
FIGS. 6A and 6B show the results of the measurements of the insertion loss of a material under test, using a material characterization system setup, wherein the material under test is subjected to a dual edge treatment, and each edge treatment comprises two materials.
Figure 6B:
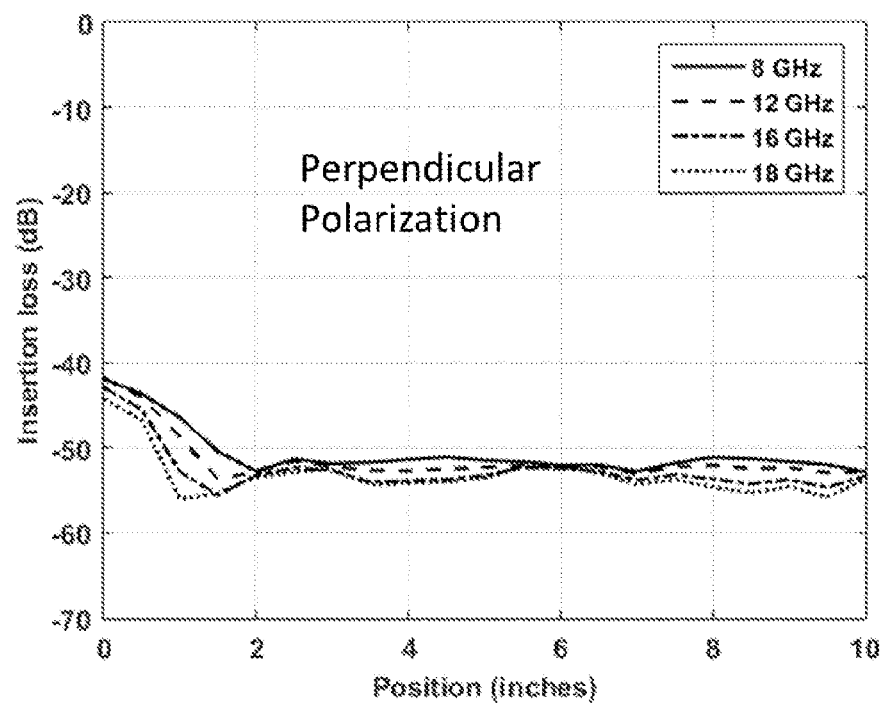

FIGS. 6A and 6B show the results of the measurements of the insertion loss of sample 12 using a setup of material characterization system 10 corresponding to the preferred configuration as described above with reference to FIG. 5. Thus, the edge treatment consists of a rectangular absorber material 30a adhered to an aluminum rectangular plate 26a and a rectangular absorber material 30b adhered to an aluminum rectangular plate 26b. The spacing between absorber material 30a and 30b is approximately 0.25 inches.

In addition and according to the previous description in reference to FIG. 5, edge 23 is substantially parallel to both edge 27b of material 26a and edge 29b of material 26b. Moreover, materials 26a and 26b overlap sample 12, such that the distance from edge 23 to the projected line of edges 27b and 29b over sample 12 is approximately 0.5 inches. Likewise, sample 12 consists of a 24-inch wide by 48-inch long rectangular substrate film of approximately 10 mils in thickness, with a rectangular cross-sectional profile, comprising a coating layer of ITO of about 0.2 mils, measured over the set of 8; 12; 16; and 18 GHz frequencies.

The results show that the measured insertion loss is significantly more uniform and consistent with the expected values corresponding to the measurements at a region around the center of sample 12, as compared to the results shown in FIGS. 2A and 2B where no edge treatment is used. In this case, sample 12 is moved along its width from a position wherein antennas 14 and 16 align with edge 27b and edge 30a (zero position) to a region around the center of sample 12, wherein the spot size of antennas 14 and 16 on sample 12 does not interact with any edges of sample 12.

More specifically, FIG. 6A shows that for parallel polarization there is no significant impact of the edge effects on these measurements as compared to the distorted measurements for distances from 0 to 3 inches, shown in FIG. 2A. Similarly, FIG. 6B shows that for perpendicular polarization, the measured non-uniform region of sample 12 is reduced from about 4 inches, as shown in FIG. 2B, to about 2 inches from position zero or approximately 2.5 inches from edge 23 of sample 12. This provides strong evidence of the significant mitigation of the adverse edge effects by using the dual edge treatment, consisting of a conductive-absorbing material combination as described, especially near the edges of sample 12.

Those skilled in the art will realize that edge treatment materials 26a, 26b, 30a, and 30b each may have alternative and different cross-sectional profiles and shapes, including circular, elliptical, triangular, polygonal, or even irregular shapes. In particular, a rectangular shape may be modified by cutting off an area of such rectangular shape.

Figure 7A:
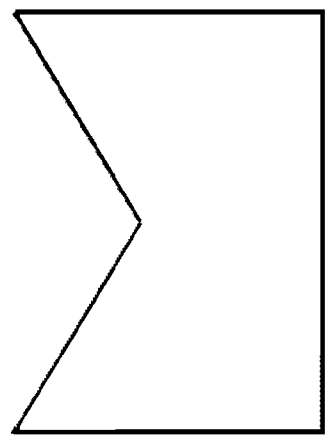
FIGS. 7A to 7C show a top view of various examples of a serrated edge that may be implemented in an edge treatment material.
Figure 7B:
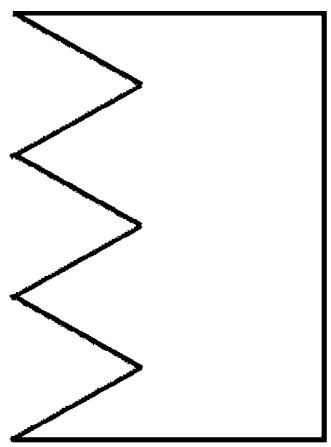
Figure 7C:
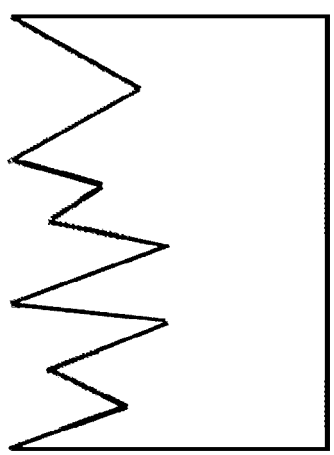

As an example, FIGS. 7A to 7C show a top view of various configurations of a serrated edge created by cutting off one or more triangles from a rectangle. In a preferred configuration, a serrated edge treatment material is disposed substantially parallel to the material under test. More preferably, the serrated edge is at least partly overlapping the material under test. Most preferably, the non-serrated edge opposite the serrated edge is non-overlapping and parallel to the edge of the material under test.

Serrated edges may help to reduce the diffraction effects from an electromagnetic wave impinging upon such edge, as well-known in the prior art. More specifically, FIG. 7A is representative of a rectangular area with a single triangular cutoff. FIG. 7B shows multiple uniform triangular cutoffs on one edge of a rectangular area. FIG. 7C illustrates the corresponding edge with multiple non-uniform triangular cutoffs. In addition, edge serration may allow a setup having a larger separation between edge treatment materials or access to measure a region of the material under test closer to its edge, which may be important in some applications.

Preferably, the cut off edge treatment is positioned such that the material under test is evaluated in areas where the cutoff is closer to the non-serrated edge opposite the serrated edge of the serrated edge treatment material.

Figure 8:
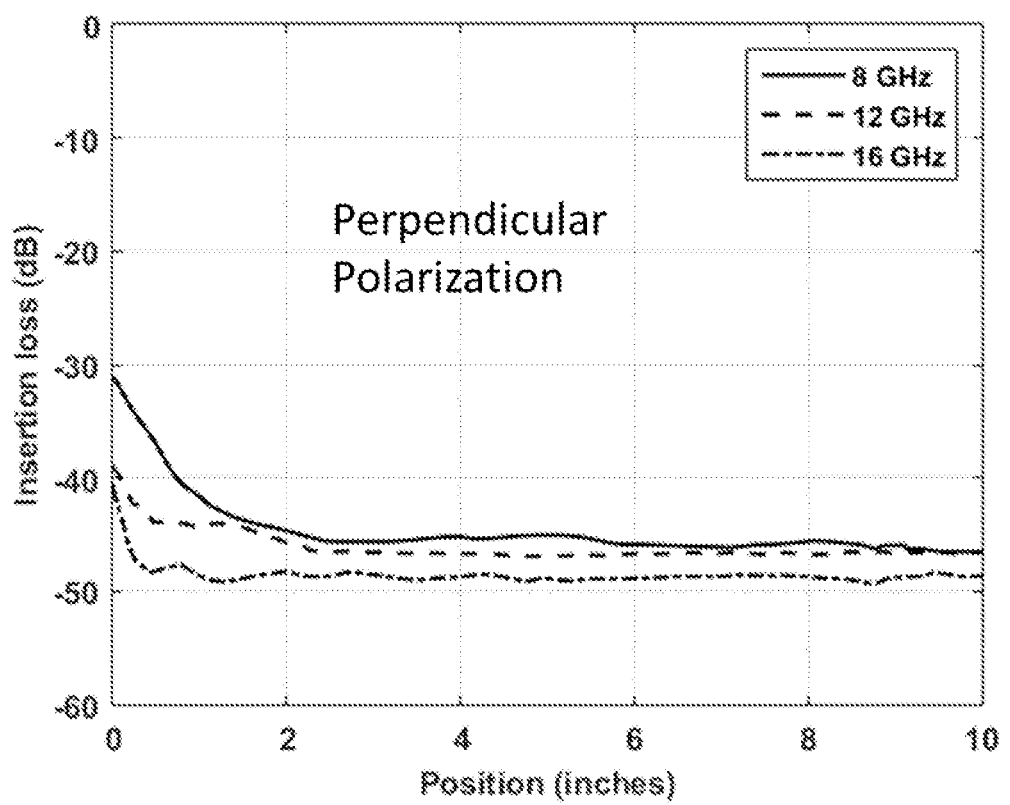
FIG. 8 shows the results of the measurements of the insertion loss of a material under test, using a material characterization system setup, wherein the material under test is subjected to a dual edge treatment, and each edge treatment has a triangular cutoff.

FIG. 8 shows the measurement results of sample 12 for a preferred configuration of an edge treatment with a single triangular cutoff, corresponding to FIG. 7A, using a setup of material characterization 10, for perpendicular polarization. The results show the insertion loss of sample 12 as a function of distance from a position wherein antennas 14 and 16 align where the cutoff is closer to the non-serrated edge opposite the serrated edge of the serrated edge treatment material (zero position) to measurement points along the width of sample 12.

In this configuration, a shape corresponding to an isosceles triangle, having a 3-inch base (unequal side) and a 1-inch height, is cut off from the rectangular-shaped edge treatment materials 26a, 26b, 30a, and 30b described in reference to FIG. 5. Thus, the non-serrated edge opposite the serrated edge of the serrated edge treatment material shown in FIG. 7A is substantially parallel to both edge 23 of sample 12 and the base of the cutoff triangle. The separation between materials 30a and 30b is approximately 1 inch, and edge treatment materials 26a and 26b partly overlap sample 12, such that the distance from edge 23 to the zero position is approximately 0.1 inches.

The results show uniform values of insertion loss at distances less than 2 inches away from edge 23 of sample 12 in the 8 to 16 GHz frequency range. Comparatively, if no edge treatment is used in this setup, the insertion loss measurements might be severely distorted up to approximately 4 inches away from edge 23, as shown in FIG. 2B. Likewise, for a dual straight-edge treatment setup with a 0.25-inch gap between materials 30a and 30b, even though such gap is substantially smaller than 1 inch, the measurements are affected at around 2.5 inches from edge 23, as shown in FIG. 6B.

Importantly, a serrated-edge configuration of edge treatment materials allows access to measure sample 12 at a closer distance to edge 23 than for the case of using a straight-edge configuration with the same setup, because less overlapping between sample 12 and edge treatment materials is required for a given gap between sample 12 and edge treatment materials. Accordingly, for a specific overlapping between sample 12 and edge treatment materials, a larger gap between sample 12 and edge treatment materials may be used when using a serrated-edge configuration instead of a straight-edge configuration.

Those skilled in the art will also realize that other combinations of materials 26a and 30a or materials 26b and 30b may be implemented, including the use of multiple layers of the same or different type of materials as part of a first or second edge treatment, either in physical contact or not with sample 12. Moreover, different configurations of materials 26a, 26b, 30a, and 30b may be used, having sharp edges, smooth edges, corrugations, or rolled edges to mitigate the propagation of an electromagnetic wave traveling or impinging on such materials.

Likewise, sample 12 may consist of a single layer or multiple layers of one or more types of material, ranging in thickness from 2 mils to 1 inch. In particular, an edge treatment configuration comprising a thin layer of a conductive material sandwiched in between two layers of a magnetic absorber material, such as the Emerson & Cuming ECCOSORB MCS, will significantly diminish an electromagnetic surface wave that would propagate along such conductive material. Alternatively, a sample under test may have a non-planar configuration.

The different configurations described above illustrate some applications of an edge treatment system for evaluation of a material using material characterization system 10. Those skilled in the art will recognize that edge treatment of a material may be useful to evaluate such material, using transmitted electromagnetic waves, wherein edge effects of the sample under test may affect general purpose measurements, system calibration, or material characterization in a frequency range extending from 0.1 GHz to 70 GHz.

Figure 9:
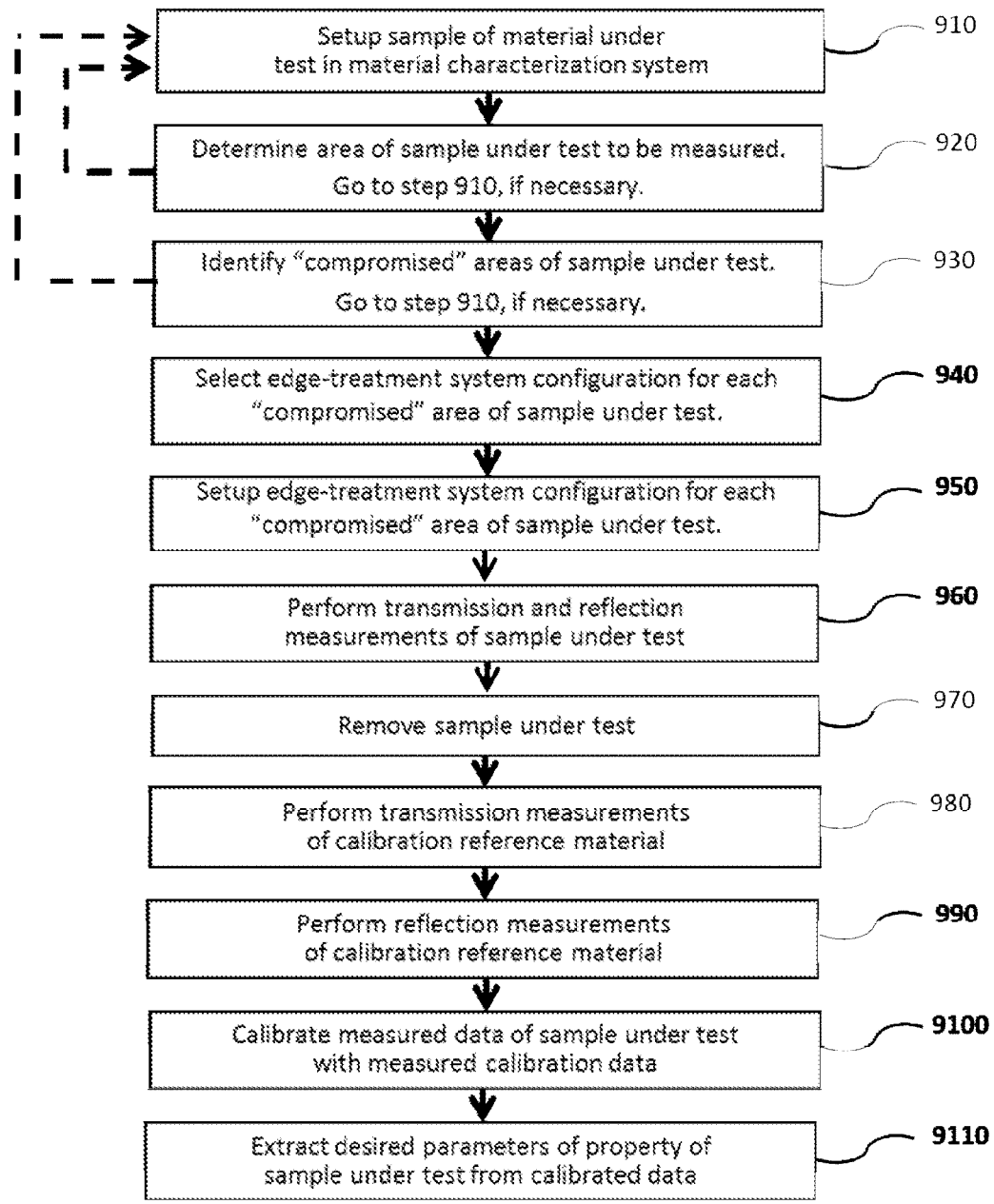
FIG. 9 shows a schematic view of a method for determining the setup of an edge treatment material for a material under test.

Regarding each of the above-described configurations, a method depicted in FIG. 9 for improving the accuracy of measurements of a sample of a material under test, especially near the edges of such sample, using an electromagnetic waves-based material characterization system, may be performed according to the following:

1. At step 910, setting up a sample of a material under test by positioning such sample on the measurement tray or mounting mechanism of the material characterization system, located in between a transmit antenna and a receive antenna, according to the desired area of the sample to be measured.

2. Next, at step 920, determining the scanning area of the material under test to be scanned by the material characterization system measurement antennas, according to distance from the sample to the transmit and receive antennas, the spot size of each of the antennas on the sample, the frequency band of the measurements, and the range of motion that the sample would be subjected to by the material characterization system during measurements. Go to step 910 if necessary to adjust the distance from the sample to the antennas, and replace the antennas or adjust the spot size of the antennas as necessary.

3. Next, at step 930, identifying each "compromised" area of the sample under test that will be scanned during measurements. A "compromised" area includes a region of the scanning area within a wavelength, at the largest frequency of the transmitted electromagnetic waves, of the edges of the sample.

4. Next, at step 940, selecting the edge treatment system configuration, such as single or dual-side, single or multi-layer, straight-edge, or serrated-edge of the edge treatment material, considering the separation and overlapping between sample and edge treatment material, and according to the closeness to the edge of the sample and the accuracy of the measurements, for each of the "compromised" areas of the sample under test identified in step 930.

5. Next, at step 950, setting up the edge treatment system configuration for each of the "compromised" areas identified in step 930, by inserting the sample under test into the edge treatment system or applying the edge treatment system directly onto the sample.

6. Next, at step 960, performing measurements and data recording of electromagnetic waves transmitted (S12 or S21 parameter evaluation) through the sample under test and electromagnetic waves reflected (S11 or S22 parameter evaluation) from the sample under test for the desired area of the sample and frequency band of interest.

7. Next, at step 970, removing only the sample under test and leaving all of the rest of the set up intact including the edge treatment material.

8. Next, at step 980, performing calibration measurements and data recording of electromagnetic waves reflected (S11 or S22 parameter evaluation) from and transmitted (S12 or S21 parameter evaluation) through a reference material, typically air, for the frequency band of interest. In case that a reference material other than air is used, such reference material should be positioned without altering the setup used for the measurements of the sample under test. This means maintaining the edge treatment material in place and positioning the reference material, preferably having the same thickness as the sample under test, at the same location of the sample under test during the measurements of the sample under test.

9. Next, at step 990, performing calibration measurements and data recording of electromagnetic waves reflected (S11 or S22 parameter evaluation) and transmitted (S12 or S21 parameter evaluation) from a reference material, typically a metal plate, positioned at the same distance from the transmit antenna as the sample under test, for the frequency band of interest. In case that a reference material other than a metal plate is used, such reference material should be positioned without altering the setup used for the measurements of the sample under test. This means maintaining the edge treatment material in place and positioning the reference material, preferably having the same thickness as the sample under test, at the same location of the sample under test during the measurements of the sample under test.

10. Next, at step 9100, calibrating measured data of the sample under test with calibration data from the measurements of the reference materials as well-known to those skilled in the art.

11. Last, at step 9110, extracting desired parameters corresponding to one or more properties of the sample of the material under test, by performing data processing and evaluation of calibrated data.

Those of ordinary skill in the art will recognize that the steps above indicated can be correspondingly adjusted for specific configurations and other constraints such as measurement equipment, operating frequency band, type of antennas, operational conditions, reference materials, surrounding environment, and available area and location for implementation of the material characterization system for a given application. In particular, the order in which the steps above indicated is performed may be accomplished in multiple ways.

More specifically, the order of the calibration measurements (steps 980 and 990 above) may be switched, and the measurements of the sample under test (step 960 above) may be performed before, after, or in between calibration measurements without affecting the final results of the calibrated data, as known to those skilled in the art. Additionally, the removal of the sample under test (step 970 above) may be performed at a different step depending on at what step the calibration measurements are conducted.

The various embodiments and the method have been described herein in an illustrative manner, and it is to be understood that the terminology used is intended to be in the nature of words of description rather than of limitation. Any embodiment herein disclosed may include one or more aspects of the other embodiments. The exemplary embodiments were described to explain some of the principles of the present invention so that others skilled in the art may practice the invention. Obviously, many modifications and variations of the invention are possible in light of the above teachings. The present invention may be practiced otherwise than as specifically described within the scope of the appended claims and their legal equivalents.

We claim:

1. A system for treating an edge of a material under test to reduce a propagation of a first electromagnetic wave impinging upon said edge of said material under test, comprising:

a first substrate having a first edge disposed in between said edge of said material under test and a propagation path of said first electromagnetic wave, wherein said first edge of said first substrate partly overlaps said material under test, such that a first area of said first substrate overlaps a first area of said material under test and a second area of said first substrate extends outwards from said first area of said first substrate overlapping said first area of said material under test and beyond a projected line of said edge of said material under test onto said first substrate, and wherein said first substrate is physically structured to reduce said propagation of said first electromagnetic wave by a sufficient extent so as to enable detection of a second electromagnetic wave of interest that may propagate through said material under test by mitigating an interference to said detection of said second electromagnetic wave caused by an interaction of said first electromagnetic wave and said edge of said material under test;

wherein said first substrate comprises a substantially conductive material to reduce said propagation of said first electromagnetic wave through said first substrate.

2. The system of claim 1, wherein said first substrate comprises a material configured to substantially absorb electromagnetic energy to reduce said propagation of said first electromagnetic wave through and along said first substrate.

3. The system of claim 1, wherein said first substrate is disposed contiguous and in physical contact with said material under test.

4. The system of claim 1, wherein said first substrate comprises a planar section and wherein said planar section is disposed substantially parallel to and partly overlaps said material under test.

5. The system of claim 1, wherein said material under test comprises at least one layer having a thickness of between 2 mils and 1 inch.

6. The system of claim 1, wherein said first substrate is disposed such that a distance from said material under test to said first substrate, over said first area of said first substrate overlapping said area of said material under test, is no larger than three quarters of a wavelength corresponding to a largest frequency of said first electromagnetic wave.

7. The system of claim 1, wherein said first substrate is disposed such that a distance from said edge of said material under test to a projected line of said first edge of said first substrate onto said material under test is between a range of one twentieth of a wavelength and three quarters of a wavelength corresponding to a largest frequency of said first electromagnetic wave.

8. The system of claim 1, wherein said property of said material under test is selected from the group consisting of transmissivity, reflectivity, absorptivity, and derivatives thereof of said material under test.

9. The system of claim 1, further comprising a material characterization system, including a transmit antenna that transmits said first and second electromagnetic waves and a receive antenna intended to only receive said second electromagnetic wave that may propagate through said material under test, such that said material under test and said first substrate are disposed in between said transmit antenna and said receive antenna.

10. The system of claim 1, further comprising a second substrate having a first edge disposed in between said edge of said material under test and a propagation path of said first electromagnetic wave, wherein said first edge of said second substrate partly overlaps said material under test, such that a first area of said second substrate overlaps a third area of said material under test and a second area of said second substrate extends outwards from said first area of said second substrate overlapping said third area of said material under test and beyond a projected line of said edge of said material under test onto said second substrate, wherein said second substrate is physically structured to reduce a propagation of an electromagnetic wave that may propagate along and through said second substrate, and wherein said second substrate is disposed opposite said first substrate such that said material under test lies between said first substrate and said second substrate.

11. The system of claim 10, wherein said first substrate and said second substrate are physically integrated into a single unit.

12. The system of claim 10, further comprising a mechanical element to physically attach said first substrate and said second substrate.

13. The system of claim 10, further comprising a mechanical element engaging said first substrate and said second substrate such that the distance between said first substrate and said second substrate is adjustable between a range of 2 mils and 4 inches.

14. The system of claim 1, wherein said first edge of said first substrate has a serrated configuration.

15. A method for treating an edge of a material under test to reduce a propagation of a first electromagnetic wave impinging upon an edge of said material under test, comprising:

a. providing at least a first substrate having a first edge disposed in between said edge of said material under test and a propagation path of said first electromagnetic wave, wherein said first edge of said first substrate partly overlaps said material under test, such that a first area of said first substrate overlaps a first area of said material under test and a second area of said first substrate extends outwards of said first area of said first substrate overlapping said first area of said material under test and beyond a projected line of said edge of said material under test onto said first substrate, and wherein said first substrate is physically structured to reduce said propagation of said first electromagnetic wave by a sufficient extent so as to enable detection of a second electromagnetic wave of interest that may propagate through said material under test by mitigating an interference to said detection of said second electromagnetic wave caused by an interaction of said first electromagnetic wave and said edge of said material under test;

b. setting up a sample of said material under test by positioning said sample on a mounting structure located in between a transmit antenna that transmits said second electromagnetic wave and a receive antenna intended to only receive said second electromagnetic wave that may propagate through said material under test;

c. determining a scanning area of said sample of said material under test;

d. identifying a compromised area of said scanning area of said sample of said material under test to be measured, wherein said compromised area is a region within a wavelength, corresponding to a largest frequency of said first electromagnetic wave, of said edge of said material under test;

e. selecting a system configuration of said first substrate for said compromised area, wherein said system configuration comprises at least one of single-side edge treatment, dual-side edge treatment, single layer edge treatment, multilayer edge treatment, straight-edge edge treatment, and serrated-edge edge treatment; and f. setting up said system configuration of said first substrate on said compromised area by one of (i) inserting said sample under test into an edge treatment system, and (ii) applying said system configuration directly onto said sample.

16. The method of claim 15, further comprising:

g. measuring and recording an amplitude, a phase, and a frequency of said second electromagnetic wave that may propagate through said sample of said material under test and an amplitude, a phase, and a frequency of a third electromagnetic wave reflected from said sample of said material under test;

h. replacing said sample of said material under test with a first reference material, wherein no other alteration of a measurement setup is performed;

i. measuring and recording an amplitude, a phase, and a frequency of a fourth electromagnetic wave that may propagate through said first reference material;

j. replacing said first reference material with a second reference material, wherein no other alteration of said measurement setup is performed;

k. measuring and recording an amplitude, a phase, and a frequency of a fifth electromagnetic wave reflected from said second reference material;

l. calibrating at a same frequency said measured amplitude and said measured phase of said second electromagnetic wave that may propagate through said sample of said material under test with said measured amplitude and said measured phase of said fourth electromagnetic wave that may propagate through said first reference material; and m. calibrating at a same frequency said measured amplitude and said measured phase of said third electromagnetic wave reflected from said sample of said material under test with said measured amplitude and said measured phase of said fifth electromagnetic wave reflected from said second reference material.

17. The method of claim 15, further comprising the step of extracting a desired parameter corresponding to at least one property of said sample of said material under test, by processing a set of measured data.

18. The method of claim 15, wherein said scanning area of said sample of said material under test is determined according to a range of motion of said sample during a measurement, a spot size of said transmit antenna on said sample, and a spot size of said receive antenna on said sample, in a frequency range of said measurement.

19. The method of claim 15 wherein said system configuration of said first substrate is selected according to a separation between said sample of said material under test and said first substrate and an overlapping between said sample of said material under test and said first substrate.

* * * * *